US010883134B2

(12) United States Patent
Jung et al.

(10) Patent No.: US 10,883,134 B2
(45) Date of Patent: Jan. 5, 2021

(54) METHOD FOR DETECTING, IDENTIFYING, OR COUNTING MICROORGANISMS, AND SYSTEM USING SAME

(71) Applicant: ALIGNED GENETICS, INC., Gyeonggi-do (KR)

(72) Inventors: Neoncheol Jung, Gyeonggi-do (KR); Keunchang Cho, Seoul (KR)

(73) Assignee: Aligned Genetics, Inc., Gyeonggi-do (KR)

( * ) Notice: Subject to any disclaimer, the term of this patent is extended or adjusted under 35 U.S.C. 154(b) by 0 days.

(21) Appl. No.: 15/570,584

(22) PCT Filed: Apr. 30, 2016

(86) PCT No.: PCT/KR2016/004573
§ 371 (c)(1),
(2) Date: Feb. 17, 2018

(87) PCT Pub. No.: WO2016/175626
PCT Pub. Date: Nov. 3, 2016

(65) Prior Publication Data
US 2018/0291420 A1   Oct. 11, 2018

(30) Foreign Application Priority Data

Apr. 30, 2015  (KR) .................. 10-2015-0061723

(51) Int. Cl.
| C12Q 1/06 | (2006.01) |
| G01N 1/30 | (2006.01) |
| C12M 1/34 | (2006.01) |
| C12M 1/10 | (2006.01) |
| G01N 33/569 | (2006.01) |
| G01N 15/06 | (2006.01) |
| G01N 15/14 | (2006.01) |
| G01N 33/58 | (2006.01) |
| G01N 33/533 | (2006.01) |
| G01N 21/64 | (2006.01) |
| G01N 15/10 | (2006.01) |
| G01N 35/04 | (2006.01) |

(52) U.S. Cl.
CPC ............... *C12Q 1/06* (2013.01); *C12M 1/10* (2013.01); *C12M 1/34* (2013.01); *C12M 41/36* (2013.01); *G01N 1/30* (2013.01); *G01N 15/06* (2013.01); *G01N 15/1434* (2013.01); *G01N 15/1463* (2013.01); *G01N 21/6428* (2013.01); *G01N 33/533* (2013.01); *G01N 33/569* (2013.01); *G01N 33/56911* (2013.01); *G01N 33/582* (2013.01); *G01N 2015/0693* (2013.01); *G01N 2015/1006* (2013.01); *G01N 2015/144* (2013.01); *G01N 2015/1486* (2013.01); *G01N 2035/0449* (2013.01)

(58) Field of Classification Search
None
See application file for complete search history.

(56) References Cited

U.S. PATENT DOCUMENTS

| 4,066,414 | A | * | 1/1978 | Selby | .................... | B01L 3/5021 |
| | | | | | | 422/549 |
| 2003/0049708 | A1 | * | 3/2003 | Crouch | ................. | C12Q 1/008 |
| | | | | | | 435/21 |
| 2010/0297659 | A1 | * | 11/2010 | Yoo | .................. | G01N 35/00029 |
| | | | | | | 435/6.16 |
| 2012/0276575 | A1 | * | 11/2012 | Fattinger | ............... | B01L 3/5025 |
| | | | | | | 435/29 |

FOREIGN PATENT DOCUMENTS

| JP | 3441779 | | 9/2003 |
| JP | 2005-261337 | | 9/2005 |
| JP | 2014-102227 | | 6/2014 |
| JP | 2014102227 A | * | 6/2014 |
| KR | 10-2011-0091719 | | 8/2011 |
| WO | WO 2010/062349 | | 6/2010 |

OTHER PUBLICATIONS

Sakura Cyto-Tek Centrifuge User Manual; 2008 (Year: 2008).*
Silva et al. 2014 (Visualizing aquatic bacteria by light and transmission electron microscopy; Antonie van Leeuwenhock 105: 1-14) (Year: 2014).*
OSU LTB Laboratories Procedure (2014); pp. 1-3 (Year: 2014).*
International Search Report PCT/KR2016/004573 (WO 2016/175626) (2016) (4 pages).
English Translation of the International Search Report PCT/KR2016/004573 (WO 2016/175626) (2016) (3 pages).
Written Opinion of the International Searching Authority PCT/KR2016/004573 (WO2016/175626) (2016) (8 pages).

* cited by examiner

*Primary Examiner* — Mary Maille Lyons
(74) *Attorney, Agent, or Firm* — Mintz Levin Cohn Ferris Glovsky and Popeo, P.C.

(57) ABSTRACT

The present invention relates to a method capable of detecting, identifying or counting microorganisms, and a system using the same, and provides a method capable of identifying, detecting or counting microorganisms in a more rapid, accurate and convenient manner than a conventional method for identifying, detecting or counting microorganisms. According to the present invention, it was found that identification, detection or counting of microorganisms can be performed in a rapid, accurate and convenient manner, when a fluorescently labeled microorganism sample is centrifuged and attached to the surface of a slide, followed by analysis of fluorescent images. Therefore, the method and system of the present invention can be useful in various fields requiring detection, identification and counting of microorganisms.

19 Claims, 7 Drawing Sheets

A: white LED for bright field image
B: iris
C: microchip
D: motorized xy-stage for chip movement
E: stepping motor
F: x10 objective lens
G: piezoelectric motor
H: filter cube
J: CCD camera K: pinhole
L: LED
M: focusing lens
N: excitation filter
O: iris
P: dichroic mirror
Q: emission filter
R: embedded controller

FIG. 8

| Bacteria | For colony | | DC | Concentration (x 10⁹/ml) | |
|---|---|---|---|---|---|
| | Temp. (°C) | Time (hr) | | CFU | Corr. (D/C) |
| *Alcaligenes faecalis* | 37 | ~24 | 0.055 | 0.047 | 1.17 |
| *Bacillus subtilis* | 30 | ~20 | 0.826 | 0.423 | 1.95 |
| *Escherichia coli* | 37 | ~20 | 1.420 | 0.910 | 1.56 |
| *Lactobacillus casei* | 30 | 24-48 | 0.264 | 0.133 | 1.98 |
| *Proteus mirabilis* | 30 | ~24 | 3.794 | 2.500 | 1.51 |
| *Serratia marcescens* | 30 | ~20 | 3.934 | 2.500 | 1.57 |

FIG. 9

METHOD FOR DETECTING, IDENTIFYING, OR COUNTING MICROORGANISMS, AND SYSTEM USING SAME

FIELD OF THE INVENTION

The present invention relates to a method capable of detecting, identifying or counting microorganisms and to a system using the same.

BACKGROUND OF THE INVENTION

The detection, identification and counting of microorganisms is a technology that is very important and widely used in biological and medical researches, clinical microbiology, cancer diagnosis and treatment, environmental science, food industry, toxicology, and related studies and industrial fields.

Particularly, in the healthcare and environmental microbiology fields, rapid detection and counting of microorganisms is very important. Pre-cultivation is necessary to detect very small amounts of microbial contamination, but conventional methods have a limitation in that they detect and count microorganisms in a time-consuming or inaccurate manner after pre-cultivation.

Methods for counting microorganisms can be largely classified into three categories: dilution methods, indirect methods, and direct methods. The dilution methods typically include a colony counting method. In this method, a pre-cultivated sample is diluted at various dilution factors, and then spread on a plurality of solid media and cultivated at a suitable temperature, after which the colonies famed are counted, thereby determining the presence and concentration of microorganisms in the pre-cultivated sample. However, for this method, information about an appropriate medium that supports the growth of a specific kind of microorganism has to be known in advance. For this reason, if cultivation conditions are unknown, this method cannot be used. For a sample containing a mixture of various kinds of microorganisms that grow under different conditions, media capable of supporting the growth of each kind of microorganism are required. Furthermore, even if cultivation conditions are well known, rapid detection and counting of microorganisms is impossible, because a time of several tens of hours to several days is taken for spread microorganisms to grow to visible colonies. In addition, in the case of microorganisms having the property of aggregating with one another or in the case in which microorganisms are aggregated due to foreign materials a sample, a single colony is not formed from a single kind of microorganism, but can be formed from a mass comprising an aggregate of various kinds of microorganisms. Thus, in this case, the results obtained indicate results different from the actual number of microorganisms. Moreover, in the case in which colonies are not formed due to damage to living microorganisms caused by a physicochemical stress that can occur during a process of spreading the microorganisms on solid media, the results obtained indicate results different from the actual number of microorganisms in the sample. Furthermore, there is a limitation in that only microorganisms capable of colonies are counted. In addition, there is a disadvantage in that the process of spreading microorganisms on a plurality of solid media is a labor-intensive and time-consuming process that has a lot of room for human error.

The indirect methods include a turbidity measurement method and an electronic cell counting method. The turbidity measurement method is a method of measuring the turbidity of a microbial suspension by a photometer, and has an advantage in that it can be easily performed. However, there are disadvantages in that this method should be performed in combination with colony counting for accurate counting, and can merely count the total number of microorganisms in the microbial suspension, but cannot differentiate between viable microorganisms and non-viable microorganisms, and the accuracy thereof is significantly low when the sample is contaminated with organic or inorganic particles other than microorganisms. In addition, in order to measure a significant level of turbidity, the concentration of microorganisms in the microbial suspension should be high. Another form of the indirect method is a method of measuring the concentration of microorganisms using current flow, and this method requires a special system and has disadvantages similar to those of the turbidity measurement method.

The direct method is a method of directly counting the number of microorganisms using a microscope. A conventional direct method is a method of directly counting microorganisms with a bright field microscope by use of a specially designed hemocytometer. This method has advantages in that it is very simple and inexpensive and can be rapidly performed. However, it requires a labor-intensive and time-consuming operation, because a number of fields should be observed using a high-magnification (e.g., 100×) objective lens in order to observe microorganisms, which are mostly several micrometers or less in size, with a bright field microscope. Furthermore, this method cannot differentiate between viable microorganisms and non-microorganisms and also cannot differentiate non-biological particles contained in a solution. Moreover, the hemocytometer designed for microbial counting has a lot of room for error. This is because a sample is prepared by inoculating a microbial suspension on a slide and then covering the microbial suspension with cover glass, and thus the volume of the microbial suspension is not accurately controlled. Another form of the direct method is a smear counting method. In this method, a microbial suspension is smeared and dried on slide glass, after which it is observed with a microscope without being stained, or observed with a microscope after being stained by a specific method, thereby counting microorganisms. However, in this method, the volume of the microbial suspension is not accurately controlled, and there are limitations similar to those of the above-described microscopic method. Another direct method is a method that comprises applying a microbial suspension to a filter having pores smaller than the size of the microorganisms to filter the microorganisms on the filter, fluorescently staining the filtered microorganisms, and counting the stained microorganisms using a fluorescence microscope. This method is recognized as a standard method for microbial counting, and has advantages in that, because it uses fluorescent staining, it has high detection sensitivity compared to the bright field microscopic observation method, and can differentiate between viable microorganisms and non-viable microorganisms. However, this method has disadvantages in that, because the pore size distribution of the filter is not uniform and the distribution of the filtered microorganisms is very non-uniform, a large number of fields should be observed to count microorganisms (Seo et al., 2010). Among recently developed methods, there is a method that comprises placing a microbial solution in a system having a chamber, applying electricity to the system to move the microorganisms to a specific plane, fluorescently staining the moved microorganisms in a state in which the microorganisms are cultivated or not cultivated, and detecting and counting the stained microorganisms using a fluorescence microscope. However, this method has disadvantages in that an expensive system is additionally required to move the microorganisms to a specific plane by application of electricity, suitable cultivation conditions have to be known in advance when the microorganisms are to be cultivated in the chamber, and it is impossible to differentiate between the case in which colonies are formed from a single kind of microorganism and the case in which colonies are formed from various kinds of microorganisms. In addition, the impact of electrical stimulation on the detection of microorganisms has not yet been carefully studied. Thus, in order to overcome the limitations of the conventional methods as described above and to count microorganisms in a simple and accurate manner, it has been constantly required to develop a method capable of directly counting the number of microorganisms in a sample.

At present, as optics and electrical/electronic engineering develop, information about cells is automatically obtained using a cell counter system, unlike the past when information on cells (e.g., the number and morphology of cells) was visually observed through a microscope. A conventional cell counting method is labor-extensive and time-consuming, and uses a hemocytometer having a configuration in which slide glass with counting grids is separated from cover glass that is placed above the slide glass. For this reason, it is difficult to accurately control the volume of a microbial solution. This causes a lot of error. In an attempt to overcome this disadvantage, various automated cell counters have recently been developed. In such automated cell counters, a cell solution is applied to a disposable metering chamber slide and imaged microscopically, and then the number of cells in the cell solution is automatically determined and the concentration thereof is calculated. However, these cell counters have been developed for the purpose of counting yeast cells or mammalian cells having a size of about 5 μm or more, and thus use low-magnification (usually 4× or less) objective lenses and have low optical efficiency. For this reason, these cell counters have a limitation in that they cannot be used to count microbial cells having a size of 5 μm or less.

Accordingly, the present inventors have made extensive efforts to develop a method capable of identifying, detecting or counting microorganisms in a more rapid, accurate and convenient manner than a conventional method for identifying, detecting or counting microorganisms. As a result, the present inventors have found that, when a fluorescently labeled microbial sample is applied to a slide including a metering chamber and is centrifuged to attach the microorganisms to the focal plane of the slide, followed by microscopic analysis of a fluorescent image, the microorganisms can be identified, detected or counted in a rapid, accurate and convenient manner, thereby completing the present invention.

DISCLOSURE

Technical Problem

Therefore, it is an object of the present invention to provide a method capable of detecting, identifying or counting microorganisms using a fluorescent or luminescent label, a metering chamber slide, a centrifugal means and an imaging means.

Another object of the present invention is to provide a system capable of detecting, identifying or counting microorganisms using the method.

Other objects and advantages of the present invention will be more clearly understood from the following description, the appended claims and the accompanying drawings.

Technical Solution

In accordance with one aspect of the present invention, there is provided a method for detecting, identifying or counting microorganisms, comprising:
(a) contacting a sample solution containing microorganisms with a fluorescent or luminescent substance capable of labeling the microorganisms;
(b) loading the sample solution, brought into contact with the fluorescent or luminescent substance, into a metering chamber disposed on the surface of a slide;
(c) centrifuging the slide, having the metering chamber disposed thereon, by a centrifugal means;
(d) acquiring a fluorescent or luminescent image from the metering chamber, disposed on the slide surface, by an imaging means; and
(e) analyzing the fluorescent or luminescent image, thereby detecting, identifying or counting the microorganisms contained in the sample solution.

Hereinafter, the present invention will be described in further detail.

(a) Contacting a Sample Solution Containing Microorganisms with a Fluorescent or Luminescent Substance Capable of Labeling the Microorganisms As used herein, the term "sample solution containing microorganisms" means either a liquid medium itself when microorganisms were cultured in the liquid medium, or a microbial suspension when microorganisms were cultured on a solid medium. The sample solution containing microorganisms may be used after being diluted or concentrated depending on the concentration of the microorganisms. As used herein, the term "contacting" means placing the sample solution containing microorganisms and the fluorescent or luminescent substance in a single container so as to allow a reaction to occur between the microorganisms and the fluorescent or luminescent substance. Specifically, the fluorescent or luminescent substance may be added to the sample solution containing microorganisms, or the sample solution containing microorganisms may be added to a solution containing the fluorescent or luminescent substance.

For labeling of microorganisms, a chromogenic, fluorescent or luminescent substance may be used. In particular, a fluorescent or luminescent substance may advantageously be used in order to increase detection sensitivity. Specifically, fluorescent dyes such as 4',6-diamidino-2-phenylindole (DAPI), SYBR gold, acridine orange (AO), BacLight, MycoLight, SYTO dyes, propidium iodide (PI) and the like may be used which can stain nucleic acids in organisms, but is not limited thereto. In addition, thiazole-based dyes may also be used which specifically stains viable microorganisms. Specifically, AO, BacLight, MycoLight or SYTO dyes may be used to specifically stain viable microorganisms, and other dyes may be used to stain non-viable microorganisms, but the scope of the present invention is not limited thereto.

Furthermore, for labeling of microorganisms, fluorescence in situ hybridization (FISH) method may be used. The FISH method is commonly used to identify microorganisms by contacting a species-specific nucleic acid probe with the microorganisms, and thus the use of the FISH method makes it possible not only to identify microorganisms, but also to detect or count microorganisms. In addition, for labeling of microorganisms, a species-specific antibody may also be used. Specifically, a fluorophore-conjugated species-specific antibody may be brought into contact with microorganisms to determine the presence or absence of a specific antigen, thereby identifying the microorganisms. Furthermore, a luminescent substance may be used to detect viable microorganisms. For example, luciferase may be used to measure ATP activity, thereby detecting viable microorganisms, but the scope of the present invention is not limited thereto.

In one example of the present invention, various kinds of microorganisms were stained with the nucleic acid staining dye MycoLight, thereby detecting and counting the microorganisms.

Meanwhile, in order to inhibit the growth of microorganisms while maintaining the viability of the microorganisms, biological buffer such as phosphate buffered saline or Tris-buffered saline may be used. In addition, biological buffer may contain a non-ionic detergent such as Triton X-100, Tween-20 or NP-40, or a chelating agent such as EDTA, EGTA or the like, so that labeling with the fluorescent or luminescent substance can be effectively achieved.

(b) Loading the Sample Solution, brought into Contact with the Fluorescent or Luminescent Substance, into a Metering Chamber Disposed on the Surface of a Slide The metering chamber that is used in the present invention serves to load a predetermined volume of the sample solution in order to detect, identify or count microorganisms, and may be manufactured in various configurations. For example, the metering chamber may be manufactured such that it includes an upper plate and a lower plate and the depth of a chamber interior formed by coupling of the upper plate with the lower plate becomes 1 to 200 μm, but not limited thereto. In addition, the metering chamber may also be manufactured such that it can control the volume of a solution that is received in the chamber.

(c) Centrifuging the Slide, Having the Metering Chamber Disposed Thereon, by a Centrifugal Means The centrifugal means that is used in the present invention serves to centrifuge the slide, and is not limited to a particular device. A commercially available centrifuge may be used, and a specially manufactured centrifuge or the like may also be used. In addition, the centrifuging is characterized in that a centrifugal force acts in a direction perpendicular to the lower plate of the metering chamber loaded with the mixture to thereby form a focal plane. The focal plane may be formed by a process in which the microorganisms contained in the mixture loaded into the metering chamber form a monolayer on the lower surface of the metering chamber. As used herein, the term "focal plane" refers to the range in which a lens is in focus. In the focal plane, an image looks clear, even when a plane perpendicular to the optical axis in focusing moves along the optical axis.

(d) Acquiring a Fluorescent or Luminescent Image from the Metering Chamber, Disposed on the Slide Surface, by an Imaging Means As imaging means in the present invention, various imaging system that are generally used may be used. In order to facilitate ease of a subsequent analysis step, an automated imaging system may preferably be used, but not limited thereto. In one embodiment, an automated imaging system as shown in FIG. 6 is used. In order to image the field at various positions in a single metering chamber slide, automated X-Y stages are provided, each comprising a single LED, an excitation filter and an emission filter.

(e) Analyzing the Fluorescent or Luminescent Image, Thereby Detecting, Identifying or Counting the Microorganisms Contained in the Sample Solution To analyze the fluorescent or luminescent image, various analysis methods that are generally used may be used. For convenience of analysis, image analysis software may be used, but the scope of the present invention is not limited thereto. In an example of the present invention, the number of microorganisms per unit volume could be counted by labeling microorganisms with a fluorescent substance in order to count the microorganisms, and then acquiring a fluorescent image using an automated imaging system, processing the fluorescent image by software manufactured by the applicant, and then counting the number of particles emitting a fluorescent signal.

In addition, the method of the present invention may further comprise, after step (a), a step of mixing the sample solution, contacted with the fluorescent or luminescent substance in step (a), with a loading buffer, and step (b) may comprise loading the mixture of the loading buffer with the sample solution contacted with the fluorescent or luminescent substance, in place of the sample solution contacted with the fluorescent or luminescent substance in step (a), into the metering chamber disposed on the slide surface. As used herein, the term "loading buffer" refers to a buffer that is used to prevent phase change from being caused by sample evaporation or a change in external pressure during the process in which the sample solution contacted with the fluorescent or luminescent substance is loaded into the chamber and centrifuged. The amount of sample loaded into the metering chamber slide is a very small (several tens of μl or less), and for this reason, a separate loading buffer is required to inhibit phase change resulting from sample evaporation or a change in external pressure after loading of the sample into the metering chamber. Furthermore, the loading buffer is required so that a particular focal plane formed after centrifugation of the metering chamber slide can be maintained without being deformed by physical impact. For such purposes, a liquid having a higher viscosity and boiling point than an aqueous solution may be used. Specifically, DMSO (dimethyl sulfoxide), glycerol, polyethylene glycol (PEG) or fructose syrup may be used, but not limited thereto. In an example of the present invention, it was shown that when glycerol or DMSO was used as loading buffer, the degree of evaporation of the solution in the chamber significantly decreased as the concentration of glycerol or DMSO increased.

In accordance with another aspect of the present invention, a system for detecting, identifying or counting microorganisms, comprising:

(a) a slide having disposed on the surface thereof a metering chamber capable of receiving a sample solution containing microorganisms; and (b) a centrifugal means capable of centrifuging the slide.

In addition, the system may further comprise: (c) a light source configured to irradiate light onto the slide; (d) an imaging means configured to acquire an image produced by the light source; (e) an image processor configured to detect, identify or count microorganisms in a specific volume of the metering chamber based on the image acquired by the imaging means; and (f) a display means configured to display the results of detecting, identifying or counting the microorganisms.

In addition, the system may further comprise a fluorescent or luminescent substance capable of labeling the microorganisms.

In addition, the system may further comprise a loading buffer that is used to apply the sample solution to the metering chamber.

The system of the present invention is a system for embodying the method of the present invention as described above, and the specific contents thereof have been described above with respect to the method, and thus the description thereof will be omitted below in order to avoid excessive overlapping.

Advantageous Effects

As described above, the present invention provides a method capable of detecting, identifying or counting microorganisms by use of a centrifugal means and an imaging means, and a system using the same. Thus, the use of the method of the present invention makes it possible to detect, identify or count microorganisms in a rapid, accurate and convenient manner.

DESCRIPTION OF DRAWINGS

FIG. 8 depicts photographs showing the imaging results acquired by a cell imaging system having a plurality of fields of view.

FIG. 9 is a table comparing the results of counting bacteria by the method of the present invention with the results of counting bacteria by a spread plate method.

BEST MODE

Hereinafter, a system for identifying, detecting or counting microorganisms according to the present invention, and a system using the same, will be described in detail with reference to the accompanying drawings. The examples described below are for illustrative purposes only and are not intended to limit the scope of the present invention.

EXAMPLES

Example 1

Labeling of Microorganisms with Fluorescent Substance

Figure 1:
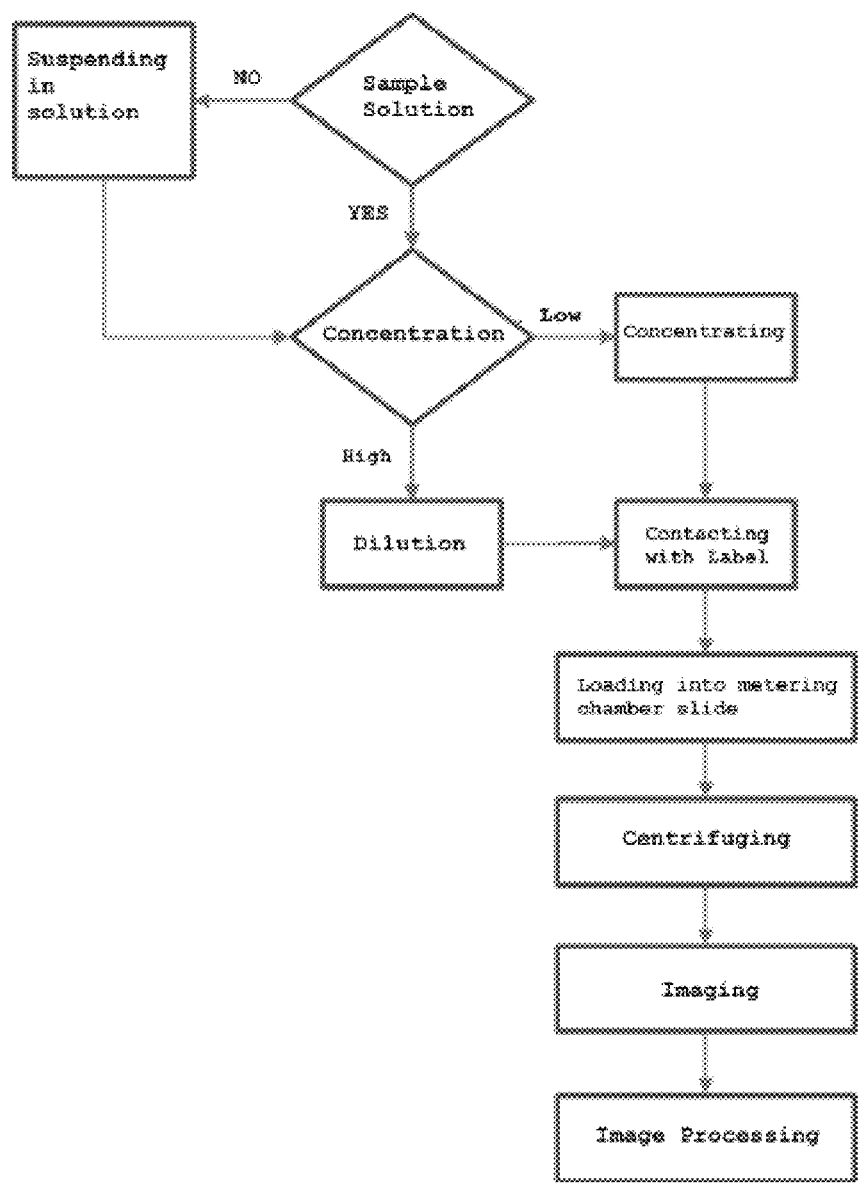
FIG. 1 is a schematic view showing the method of the present invention.
Figure 2:
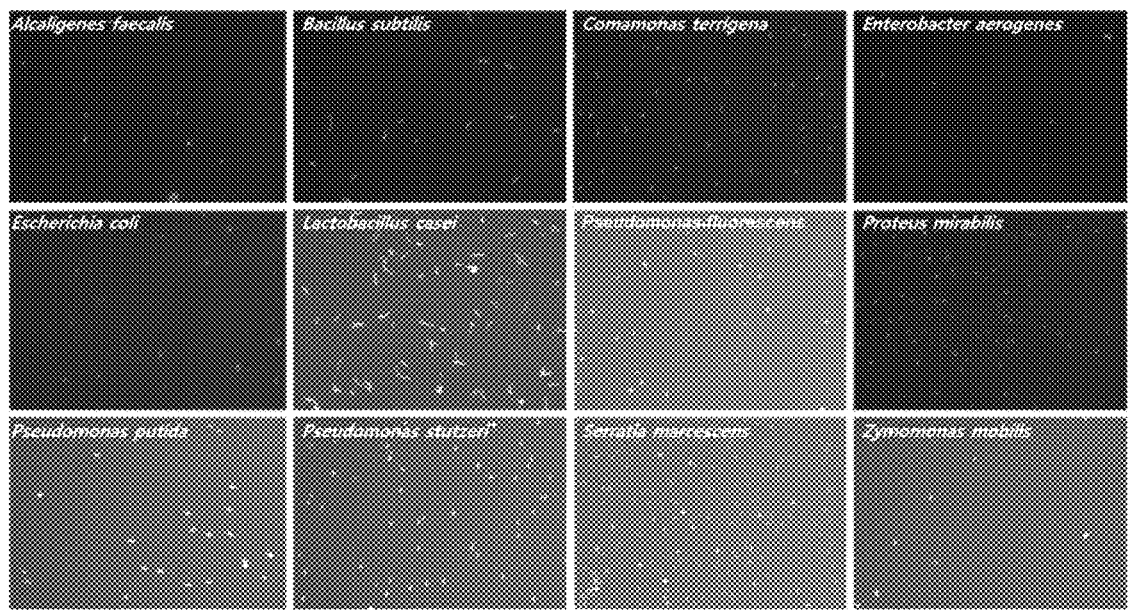
FIG. 2 depicts photographs showing the results of fluorescently imaging various kinds of microorganisms stained with a nucleic acid-staining fluorescent dye.

In order to label various microorganisms including *E. coli*, microorganisms were stained with the nucleic acid-staining dye MycoLight (ATT Bioquest, USA). Specifically, microorganisms were diluted and suspended in Dulbecco's phosphate-buffered saline (DPBS) solution at various ratios (such as 1:2 to 1:100), and the suspension of the microorganisms was brought into contact with MycoLight and allowed to react for 5 to 30 minutes so that DNA of the microorganisms would be labeled with MycoLight. As the reaction buffer, 2.5×PET (2.5 mM EDTA and 0.025% Tween-20 in 2.5×PBS) or 1×DPBS was used. FIG. 2 shows fluorescence images of various microorganisms fluorescently labeled by contact with MycoLight as described above.

Example 2

Determination of Composition of Loading Buffer

Figure 3:
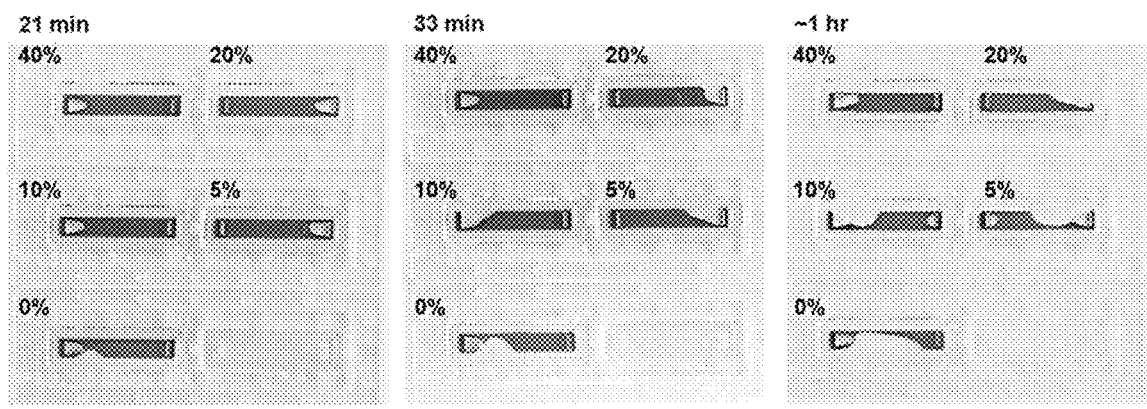
FIG. 3 depicts photographs showing the results of measuring the time-dependent evaporation of a solution loaded into a metering chamber slide.

The amount of sample loaded into the metering chamber slide is a very small (several tens of μl or less), and for this reason, a separate loading buffer is required to inhibit phase change resulting from sample evaporation or a change in external pressure after loading of the sample into the metering chamber. Furthermore, the loading buffer is required so that a particular focal plane formed after centrifugation of the metering chamber slide can be maintained without being deformed by physical impact. For such purposes, an experiment was performed in order to use glycerol (Samchun Pure Chemical Co., Ltd., Korea), DMSO (Sigma, USA) or X-clarity mounting solution (hereinafter referred to as M/S; Logos Biosystems, Inc.), which has a higher viscosity and boiling point than aqueous solution. FIG. 3 shows the results obtained by loading solutions containing various concentrations of glycerol into the 100-μm-depth chamber of a metering chamber slide, and then observing the time-dependent evaporation of the solutions while incubating the solutions at room temperature. In order to easily observe the degree of evaporation of the solutions, trypan blue dye (Life Technologies, USA) together with glycerol was added to the loaded solutions. As shown in FIG. 3, the degree of evaporation of the solutions in the chamber significantly decreased as the concentration of glycerol increased. DMSO having a higher boiling point than water also showed a similar effect. As described above, the condition where evaporation of the solution in the chamber is prevented by an additive having a high boiling point significantly inhibited the evaporation of a sample, which would occur either during sample handling before or after concentration or during centrifugation. The experimental results indicated that 80 v/v % M/S or 40 v/v % glycerol (final concentration) can be used as a loading buffer and that it is enough to perform centrifugation at 100 RCF for 10 minutes Example 3

Centrifugation of Slide

Figure 4:
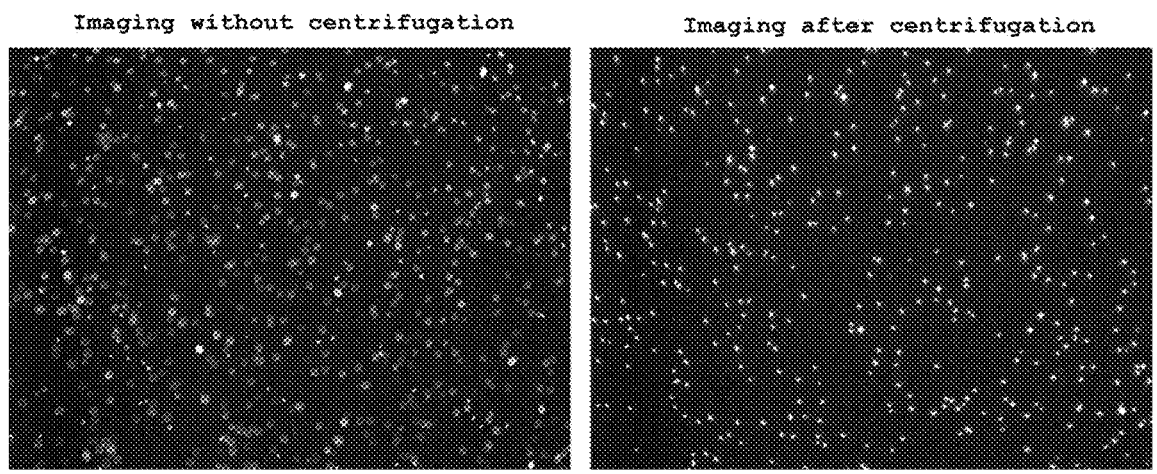
FIG. 4 depicts photographs showing the results of imaging cells without centrifugation, in comparison with the results of imaging cells after centrifugation.

In order to centrifuge the slide so as to effectively form a focal plane, the kind and concentration of loading buffer added to a sample, the posture of the metering chamber slide during centrifugation, rotating speed and time during centrifugation, etc., were examined. FIG. 4 shows images obtained by staining *E. coli* DH5α cells with a nucleic acid-staining MycoLight reagent, mixing the cells with a loading buffer (glycerol), loading 2.5 μl of the mixture into the metering chamber, and then fluorescently imaging the centrifuged slide and the non-centrifuged slide for comparison. Centrifugation was performed at 500 RCF for 30 seconds. In centrifugation, a centrifugal force acted in a direction perpendicular to the bottom of the metering chamber slide. The slide was imaged and analyzed using a digital fluorescence microscope (iRiS (trade name), Logos Biosystems, Inc.) equipped with a 10× objective lens, and as a result, it was shown that, when centrifugation was not performed, the cells were not on the same focal plane, and for this reason, all the cells could not be imaged on a specific focal plane, and a large number of the cells were imaged in an unfocused state. However, when centrifugation was performed, almost all of the cells were on a single focal plane, and almost all of the cells could be imaged on a specific focal plane.

After changing the chamber slide depth (20 μm and 100 μm), the kind of loading buffer (PBS and glycerol) and centrifugal speed (40 RCF and 900 RCF), cell deflection, focal plane formation, focal plane deviation, and cell movement were observed. The following buffer solutions were prepared and used: a buffer solution obtained by mixing 20 μl of E. coli, 4 μl of MycoLight and 16 μl of 2.5×PET and adding 40 μl of 80% glycerol to the mixture; and a buffer solution obtained by mixing 20 μl of E. coli, 4 μl of MycoLight and 56 μl of DPBS. When the slide depth was low, sample aggregation appeared after centrifugation, and in the conditions of 100-μm chamber slide depth, 40 RCF, and glycerol, about 80% of E. coli cells in the sample precipitated, and large focal plane derivation (32 μm) was formed. PBS started to dry on a 20-μm slide before centrifugation. The results are shown in Table 1 below.

The sample obtained by adding and reacting glycerol as described above was transferred to a 100-μm-depth chamber slide, centrifuged at each of 50, 100, 200 and 400 RCF for 10 minutes, and then analyzed. The results of the analysis are shown in Table 2 below. 90% or more of the sample precipitated at 100 RCF or higher, and deflection at the inlet started to appear from 100 RCF.

TABLE 1

| Slide depth | Loading buffer | Centrifuge speed | | | |
|---|---|---|---|---|---|
| | | 40 RCF | | 900 RCF | |
| | | PBS | Glycerol | PBS | Glycerol |
| 20 μm | Deflection | Moderate | None | Occurred | Occurred |
| | Focal plane deviation | None | None | None | None |
| | Sample movement | Moderate | None | Moderate | None |
| 100 μm | Deflection | Moderate | None | Occurred | Occurred |
| | Focal plane deviation | None | Occurred | None | None |
| | Sample movement | Occurred | None | Moderate | None |

TABLE 2

| RCF | Focal plane deviation (Z-axis) | Deflection (inlet) | Deflection (outlet) | Distribution deviation between the center and the edge |
|---|---|---|---|---|
| 0 | 91.2 μm | — | — | — |
| 50 | 55.13 μm | None | Slight | None |
| 100 | 18.97 μm | Slight | Occurred | Slight |
| 200 | 9.23 μm | Occurred | Occurred | Occurred |
| 400 | 8.35 μm | Occurred | Occurred | Occurred |

Figure 5:
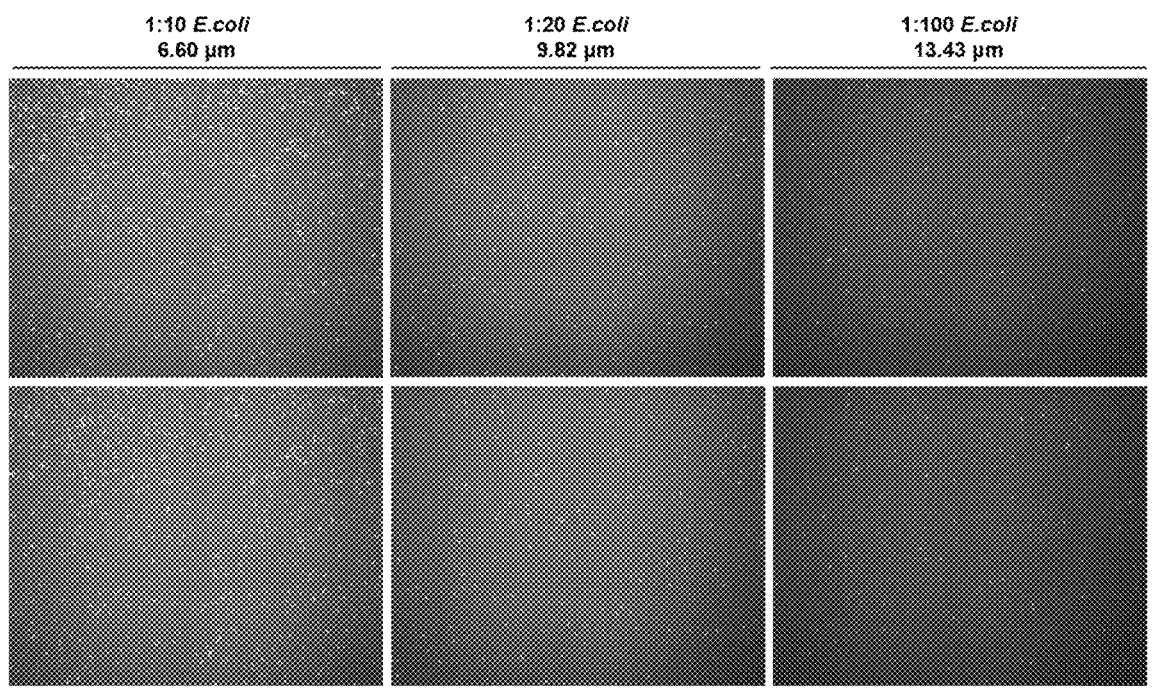
FIG. 5 shows the results obtained by loading each of 1:10, 1:20 and 1:100 of *E. coli* into a 100-μm chamber slide, centrifuging the loaded *E. coli*, and observing the centrifuged *E. coli*.
Figure 6:
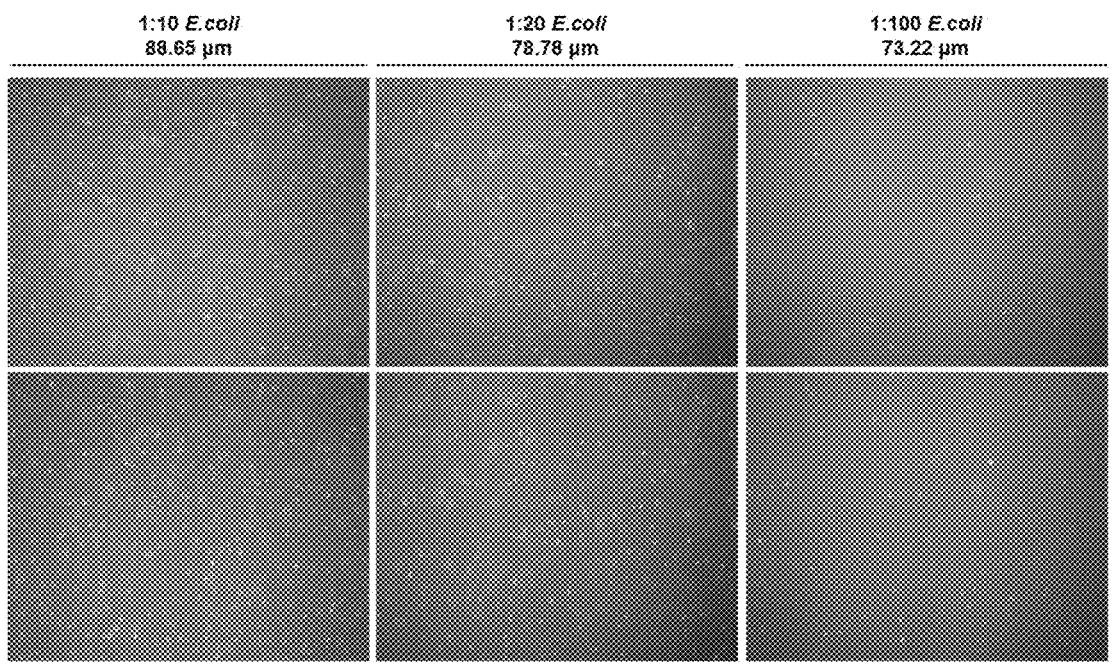
FIG. 6 shows the results obtained by loading each of 1:10, 1:20 and 1:100 of *E. coli* into a 100-μm chamber slide, and observing the loaded *E. coli* without centrifugation.

A 100-μm-depth chamber slide, a staining reagent (AAT Bioquest Cat #24001, Lot #106137) comprising a solution of 200 μM of MycoLight in DMSO, 2.5×reaction buffer (2.5×PET) (a solution of 2.5 mM EDTA and 0.025% Tween-20 in 2.5×PBS), 80% glycerol, and iRiS TC PlanFluor (Logos Biosystems, Inc.) were used. E. coli was diluted in DPBS at ratios of 1:10, 1:20 and 1:100. 10 μm microorganisms, 2 μl of staining reagent, and 2.5×PET were reacted. After 30 minutes of the reaction, 20 μl of loading buffer was added to the reaction mixture. The prepared sample was transferred to a chamber slide, and then the sample before centrifugation was compared with the sample after centrifugation. The results are shown in FIGS. 5 and 6. It could be seen that, in comparison with an image obtained without centrifugation (FIG. 6), the focal plane in an image obtained after centrifugation (FIG. 5) was uniformly formed. In addition, deflection after centrifugation was examined at varying centrifugal speeds (200, 400, 600 and 800 RCF). Furthermore, precipitation of microorganisms in the sample was analyzed while reducing the centrifugal speed. E. coli diluted at a ratio of 1:10 as described above was used, and the chamber slide was centrifuged at each of 40, 50 and 100 RCF for 10 minutes, and the results were compared. Table 3 below shows focal plane deviation.

TABLE 3

| RCF | Focal plane deviation (Z-axis) |
|---|---|
| 40 | 9.18 μm |
| 50 | 7.78 μm |
| 100 | 4.43 μm |

Example 4

Acquisition and Analysis of Fluorescent Images

Figure 7:
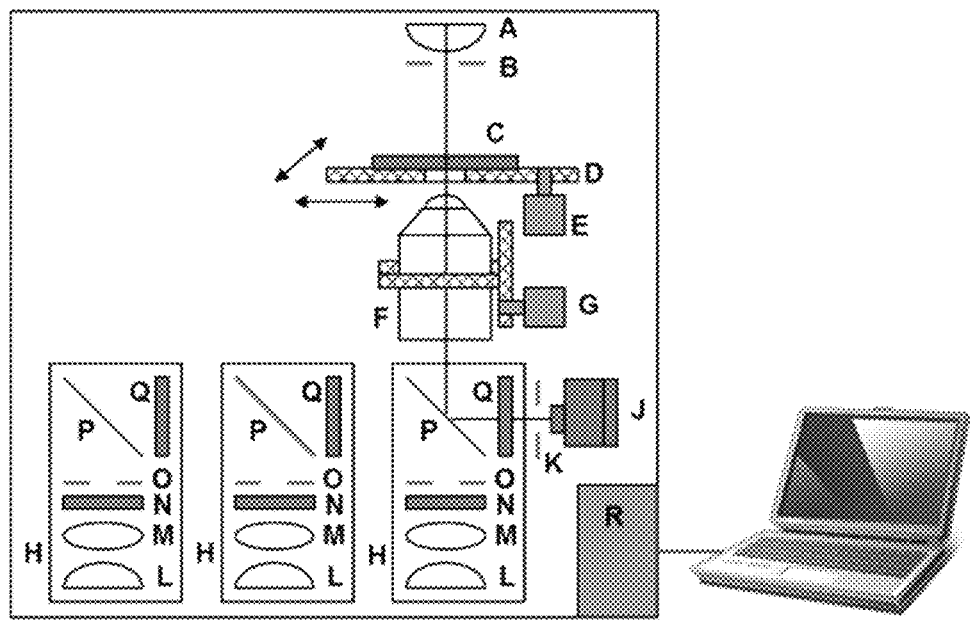
FIG. 7 is a schematic view illustrating a cell imaging system.
Figure 8:
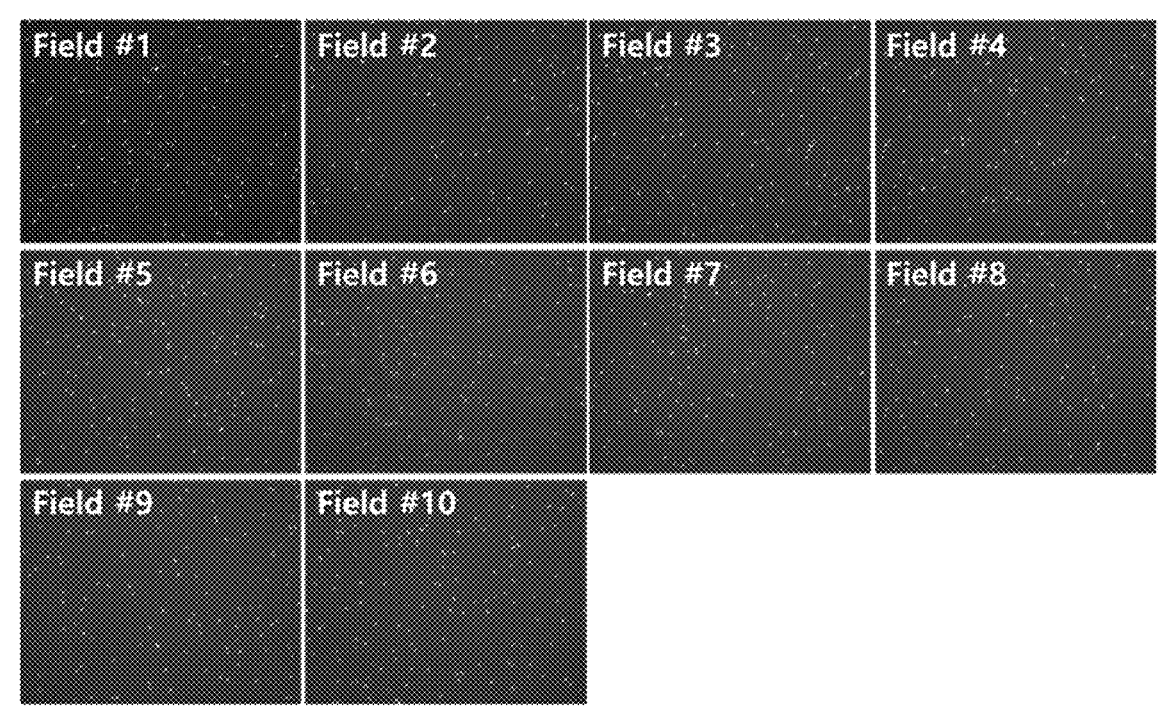

In order to acquire fluorescent images, an automated imaging system as shown in FIG. 7 was constructed. In order to image the fields at various positions in a single metering chamber slide, automated X-Y stages were constructed, each comprising a single LED, an excitation filter and an emission filter. Using this automated imaging system, images of the slide centrifuged according to the method of Example 3 were acquired (FIG. 8). The automatically acquired images were processed by image analysis software (Logos Biosystems, Inc., Korea), and then the number of particles emitting a fluorescent signal was counted, thereby determining the number of microorganisms per unit volume. The results of counting microorganisms by the method of the present invention and the results of counting microorganisms by a conventional spread plate method were comparatively analyzed (FIG. 9). In FIG. 9, DC represents the results obtained by converting the number of cells, counted using image analysis software, into concentration per unit volume (ml), and CFU (colony forming unit) represents the results obtained by converting the number of colonies, formed in spread plate culture, into the concentration of cells capable of forming colonies per unit volume (mL). Corr (correlation) is a value obtained by dividing DC (D) by CFU (C). The results of the analysis indicated that the method for counting microorganisms according to the present invention has a high correlation with the method of counting microorganisms by the spread plate method. Although there was a difference depending on the kind of loading buffer, a dye gradient was formed when the depth of the chamber on the slide was low.

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

INDUSTRIAL APPLICABILITY

As described above, the present invention can be widely used for the detection, counting and identification of small microorganisms such as bacteria, and thus can be used for the detection, counting and identification of microorganisms in various fields.

What is claimed is:

1. A device for detecting, identifying or counting microorganisms, comprising:
   (a) a slide having disposed on a surface thereof a metering chamber capable of receiving a sample solution containing microorganisms, wherein the metering chamber comprises an upper plate and a lower plate, and a chamber interior formed by coupling of the upper plate with the lower plate has a depth of 1 to 200 µm and
   (b) a centrifugal means configured to apply a centrifugal force in a direction perpendicular to the lower plate of the metering chamber containing the sample solution, thereby forming a focal plane in the metering chamber;
   (c) a light source configured to irradiate light onto the slide;
   (d) an imaging means configured to acquire an image produced by the light source;
   (e) an image processor configured to detect, identify or count microorganisms in a predetermined volume of the metering chamber based on the image acquired by the imaging means; and
   (f) a display means configured to display the results of detecting, identifying or counting the microorganisms.

2. The device of claim 1, further comprising a fluorescent or luminescent substance capable of labeling the microorganisms.

3. The device of claim 1, further comprising a loading buffer which is used to apply the sample solution to the metering chamber.

4. The device of claim 3, wherein the loading buffer comprises a substance having a higher boiling point than water.

5. The device of claim 4, wherein the substance is one or more of glycerol, DMSO, fructose syrup, and polyethylene glycol.

6. The device of claim 1, wherein the metering chamber is a chamber capable of controlling volume of the solution that is received in the chamber.

7. The device of claim 1, wherein the focal plane is formed by a process in which the microorganisms contained in the sample solution loaded into the metering chamber form a monolayer on the lower surface of the metering chamber.

8. The device of claim 1, wherein two or more of the detecting, identifying and counting of the microorganisms are capable of being performed at the same time.

9. A method for detecting, identifying or counting microorganisms using the device of claim 1, comprising the steps of:
   (i) contacting a sample solution containing microorganisms with a fluorescent or luminescent substance capable of labeling the microorganisms;
   (ii) loading the sample solution, contacted with the fluorescent or luminescent substance, into the metering chamber disposed on the surface of the slide;
   (iii) centrifuging the slide, having the metering chamber disposed thereon, by the centrifugal means;
   (iv) acquiring a fluorescent or luminescent image from the metering chamber, disposed on the slide surface, by the imaging means; and
   (v) analyzing the fluorescent or luminescent image, thereby detecting, identifying or counting the microorganisms contained in the sample solution.

10. The method of claim 9, wherein the fluorescent or luminescent substance in step (i) labels nucleic acids of the microorganisms.

11. The method of claim 9, wherein the fluorescent or luminescent substance in step (i) labels activity of viable microorganisms.

12. The method of claim 9, wherein the fluorescent or luminescent substance in step (i) is a substance conjugated to an antibody.

13. The method of claim 12, wherein the antibody labels a microorganism-specific antigen.

14. The method of claim 9, wherein the centrifuging in step (iii) is performed such that a centrifugal force acts in a direction perpendicular to the lower plate of the metering chamber loaded with the sample solution, thereby forming a focal plane.

15. The method of claim 14, wherein the focal plane is formed by a process in which the microorganisms contained in the sample solution loaded into the metering chamber form a monolayer on the lower surface of the metering chamber.

16. The method of claim 9, further comprising, after step (i), a step of mixing the sample solution, contacted with the fluorescent or luminescent substance in step (i), with a loading buffer, and step (ii) comprises loading the mixture of the loading buffer with the sample solution contacted with the fluorescent or luminescent substance, in place of the sample solution contacted with the fluorescent or luminescent substance in step (i), into the metering chamber disposed on the slide surface.

17. The method of claim 16, wherein the loading buffer comprises a substance having a higher boiling point than water.

18. The method of claim 17, wherein the substance is one or more of glycerol, DMSO, fructose syrup, and polyethylene glycol.

19. The method of claim 9, wherein two or more of the detecting, identifying and counting of the microorganisms are capable of being performed at the same time.

* * * * *